(12) United States Patent
Shinojima et al.

(10) Patent No.: US 6,325,996 B1
(45) Date of Patent: Dec. 4, 2001

(54) COMPOSITION FOR LIP ROUGE

(75) Inventors: Satoshi Shinojima; Takashi Minami; Yoshikazu Soyama; Kinya Hosokawa, all of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/549,181

(22) Filed: Apr. 13, 2000

(30) Foreign Application Priority Data

Apr. 14, 1999 (JP) .................................................. 11-106879
Oct. 15, 1999 (JP) .................................................. 11-293091

(51) Int. Cl.[7] .......................... A61K 7/025; A61K 7/021; A61K 7/00; A61K 31/695
(52) U.S. Cl. .............................. 424/64; 424/63; 424/401; 514/844
(58) Field of Search .................................. 424/69, 61, 63, 424/403, 404, 425, 64, 400, 401

(56) References Cited

U.S. PATENT DOCUMENTS 5,362,482 * 11/1994 Yoneyama et al. .................... 424/69

FOREIGN PATENT DOCUMENTS

10139630 * 5/1998 (JP) .
12-297012 * 10/2000 (JP) .
13-114648 * 4/2001 (JP) .

* cited by examiner

*Primary Examiner*—Thurman K. Page
*Assistant Examiner*—Blessing Fubara
(74) *Attorney, Agent, or Firm*—Snider & Associates; Ronald R. Snider

(57) ABSTRACT

In order to provide a composition for lip rouge, which is excellent with a light feeling has good gloss and is stable for a long time, the composition for lip rouge contains a glyceryl diisostearate/hydrogenated rosinate and/optionally a hydroxy acid ester, a heavy liquid isoparaffin, a methylphenyl polysiloxane.

7 Claims, No Drawings

COMPOSITION FOR LIP ROUGE

RELATED APPLICATIONS

This application claims the priority of Japanese Patent application No.11-106879 filed on Apr. 14, 1999 and Japanese Patent application No. 11-293091 filed on Oct. 15, 1999 which are incorporated herein by reference.

FIELD OF THE INVENTION

The present invention relates to a composition for lip rouge and, in particular, to an improvement in the long term preservation stability and improvement in gloss and feel during use.

BACKGROUND OF THE INVENTION

Generally wax and various kinds of liquid oil are combined to form a lip rouge composition. Especially, in recent years, because gloss is demanded at the time of lip application, lanolin and heavy liquid isoparaffin are applied as the oils that give gloss.

However, the smell that emanates from oxidation degradation of lanolin and the like is a problem. Especially, as there is the possibility that the composition for lip rouge may be stored for a long time with respect to the period of around sale. Moreover, the occurrence of the odor is an extremely important problem, because the rouge is applied to the lips which are close to the smell sensing areas.

Also, heavy liquid isoparaffin and the like have high viscosity. Accordingly, when it is extensively used in the composition for lip rouge, the feeling especially the spreadability is unsatisfactory.

SUMMARY OF THE INVENTION

The present invention is achieved in view of the foregoing prior art. An object of the present invention is to provide a composition for lip rouge which feels light on the lips and stable over a long period of time.

As a result of diligent study by the present inventors a composition for lip rouge has been found. A composition that has the gloss equivalent of lanolin can be obtained by combining a glyceryl diisostearate/hydrogenated rosinate and/optionally a hydroxy acid ester and a heavy liquid isoparaffin. Furthermore, the present inventors have found that the feel of the rouge on the lips is improved substantially without damage by adding methylphenyl polysiloxane.

Namely, a composition for lip rouge of the present invention contains a glyceryl diisostearate/hydrogenated rosinate and/optionally a hydroxy acid ester and heavy liquid isoparaffin and methylphenyl polysiloxane.

Also, in the present invention, it is preferable that said composition contains 5 to 20 wt % of the glyceryl diisostearate/hydrogenated rosinate, 10 to 30 wt % of the heavy liquid isoparaffin, and 10 to 30 wt % of the methylphenyl polysiloxane.

Also, in the present invention, it is preferable that said composition contains 5 to 30 wt % of the hydroxy acid ester, 10 to 30 wt % of the heavy liquid isoparaffin, and 10 to 30 wt % of the methylphenyl polysiloxane.

Also, in the present invention, it is preferable that said hydroxy acid ester is composed of an aliphatic alcohol of carbon number 12 to 20, and a hydroxy acid of carbon number 12 to 20.

Also, in the present invention, it is preferable that said hydroxy acid ester is composed of 12-hydroxystearic acid of the hydroxy acid, and 2-heptyl undecanol of the aliphatic alcohol.

Also, in the present invention, it is preferable that said heavy liquid isoparaffin's mean molecular weight is 500 to 3000.

Also, in the present invention, it is preferable that said composition is a lip rouge.

BEST MODE OF THE INVENTION

In the following, the embodiment for carrying out the present invention will be explained.

The glyceryl diisostearate/hydrogenated rosinate in the present invention has the following constitutional formula.

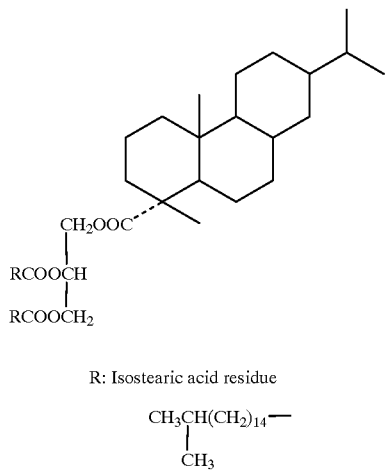

R: Isostearic acid residue $$CH_3CH(CH_2)_{14}-\underset{CH_3}{|}$$

To obtain a fine gloss the amount of said glyceryl diisostearate/hydrogenated rosinate in the composition is preferably 5 wt % or more. Also, an upper limit amount of the glyceryl diisostearate/hydrogenated rosinate is preferably 20 wt % or less. A greater amount is unfavorable because no improvement of the gloss is expected and it may become heavy and less spreadable.

The hydroxy acid ester in this invention is obtained by esterifying by the means known in the art from hydroxy acid and aliphatic alcohol. Examples of the hydroxy acid that composes the hydroxy acid ester include hydroxy lauric acid, hydroxy myristic acid, hydroxy palmitic acid, hydroxy stearic acid, ricinoleic acid, oligomer of 12-hydroxy stearic acid etc. In these, the hydroxy acid of carbon number 12 to 20 is preferable, and the hydroxy acid of carbon number 16 to 20 is even better. Also, examples of aliphatic alcohol include cetyl alcohol, stearyl alcohol, isopalmityl alcohol, oleyl alcohol, behenyl alcohol, 2-hexyldecyl alcohol, 2-octyldodecanol, 12-hydroxy stearyl alcohol etc. In these, the aliphatic alcohol of carbon number 12 to 20 is preferable and the aliphatic alcohol of carbon number 16 to 20 is even better. Especially preferred is the ester of 12-hydroxy stearic acid and 2-heptyl undecanol.

To obtain fine gloss the amount of said hydroxy acid ester in the composition is preferably 5 wt % or more. Also, the upper limit of the amount of the hydroxy acid ester is preferably 30 wt % or less. When the amount is more than 30 wt %, it is unfavorable because an improvement in gloss may not be obtained, the composition may become heavy and difficult to spread.

Also, in the present invention, the heavy liquid isoparaffin is used to improve gloss with said glyceryl diisostearate/hydrogenated rosinate and/optionally the hydroxy acid ester. The heavy liquid isoparaffin is a mixture of the long chain hydrocarbon of the saturation type that has a side chain that hydrogenated the copolymer of isobuten and n-buten. Even the double bond in terminal of the side chain is hydrogenated. A degree of polymerization of the heavy liquid isoparaffin can be changed by changing the condition of polymerization. The heavy liquid isoparaffin having mean molecular weight 500 to 3000 is desirable from the viewpoint of viscosity etc. in the present invention. The heavy liquid isoparaffin of approximately mean molecular weight 1000 is optimum. To improve gloss, the amount in the composition of said heavy liquid isoparaffin is preferably 10 wt % or more. Also, the upper limit of heavy liquid isoparaffin is preferably 30 wt % or less from relative relation with other components. It may become difficult to spread when the amount of heavy liquid isoparaffin is more than 30 wt %.

Also, methylphenyl polysiloxane is combined, to improve of the spreadability of the composition for lip rouge in the present invention. The methylphenyl polysiloxane needs to be combined 10 to 30 wt % to obtain this effect. The viscosity of the methylphenyl polysiloxane preferably is 5 to 100 cs. The point of spreadability has a tendency to feel heavy in the case where the amount is less than 10 wt %. The gloss has a tendency to become unsatisfactory in the case where the amount is more than 30 wt %.

In the present invention, as an optional component, it is possible to use hydrocarbon waxes which usually used for cosmetics. Examples are microcrystalline wax, carnauba wax, candelilla wax, polyethylene wax, ceresin wax etc. Although an amount of the hydrocarbon wax differs by the solidification power to oil, it is preferably 0.5 to 25 wt % in whole amount of the composition for lip rouge, and more preferably it is 3 to 10 wt %. In the case where the amount is less than 0.5 wt %, a shape of rouge may not be maintained. Gloss may be lost in the case where the amount is more than 25 wt %.

As occasion demands, in the range where there is no damage the effects on the object of the present invention, it is possible to include a wax, oil content, water, humectants, surfactants, pigments, resin, clay minerals, oxidation inhibitors, antiseptics, ultraviolet rays shield agent, perfume etc. in the composition for lip rouge in the present invention.

The present invention is explained in detail by the examples which follow. The following does not limit the present invention. The amount is indicated by weight percentage. The inventors did the various kinds of tests in studying the composition for lip rouge in the present invention. The effect and test method and evaluation standards are explained before the examples are set forth.

[Spreadability]

The professional panel(15 members) used the composition for lip rouge(sample) of each working example, of each comparative example, and evaluated with 5 stages (comprehensive evaluation) by sensing.

<Evaluation Standard>

1: bad spreadability (heavy)

2: slightly bad spreadability (slightly heavy)

3: normal spreadability

4: slightly good spreadability (slightly light)

5: good spreadability (light)

(Evaluation)

⊚: evaluation (mean value) 4.5 to 5.0

○: estimation (mean value) 3.5 to less than 4.5

Δ: estimation (mean value) 2.5 to less than 3.5

X: estimation (mean value) 1.5 to less than 2.5

X X: estimation (mean value) 1.0 to less than 1.5

[Gloss]

The professional panel(15 members) used the composition for lip rouge(sample) of each working example, of each comparative example, and evaluated with 5 stages (comprehensive evaluation) by sensing.

<Evaluation Standard>

1: no gloss

2: slightly no gloss

3: normal gloss

4: slightly good gloss

5: good gloss (Evaluation)

⊚: evaluation (mean value) 4.5 to 5.0

○: estimation (mean value) 3.5 to less than 4.5

Δ: estimation (mean value) 2.5 to less than 3.5

X: estimation (mean value) 1.5 to less than 2.5

X X: estimation (mean value) 1.0 to less than 1.5

[Smell]

The inventors worked an accelerating degradation test of composition for lip rouge and then evaluated the smell.

Furthermore, the acceleration degradation test was carried out by measuring oxidation degradation induction time by CDM test (Conductmetric Determination Method).

(Definition)

The sample is put to a reaction container. While heating, drying air is sent into the chamber. The volatile decomposition product that was formed by oxidation is collected in water. The time to a point of inflection when dielectric constant changes sharply, was obtained as oxidation degradation induction time. This was made the guideline for the oxidation stability of the sample.

(Method)

By using the 679 rancimat (manufactured by Metrohm), The inventors made measurements on the basis of Standard Methods for the Analysis of Fats, Oil and Related Materials 2.5.1.2.2-1996 (Japan Oil Chemists' Society). The measurements were carried out at a temperature of 120° C., and with air flow rate 20 L/h.

<Evaluation Standard>

○: Oxidation induction time is more than 48 hours

Δ: Oxidation induction time is more than 20 hours to less than 48 hours

X: Oxidation induction time is less than 20 hours

Prior Art (Glyceryl Diisostearate/Hydrogenated Rosinate Addition Composition)

First of all, the conventional composition for lip rouge of following Table 1 was prepared and each of the above-mentioned tests was carried out. The composition of Table 1 includes the examples of the conventional composition for lip rouge containing a significant amount of lanolin as the gloss component. Comparative example 1 is the composition for lip rouge that does not contain the gloss component. Comparative examples 2 to 6 are the composition for lip rouge containing lanolin as the gloss component.

TABLE 1

| Raw Material | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Ceresin wax | 12 | 12 | 12 | 12 | 12 | 12 |
| Carnauba wax | 1 | 1 | 1 | 1 | 1 | 1 |
| Glyceryl tri-2-ethylhexanoate | to 100 | to 100 | to 100 | to 100 | to 100 | to 100 |
| Lanolin | — | 10 | 10 | 10 | 10 | 10 |
| Macdemia nut oil | 10 | 10 | 10 | 10 | 10 | 10 |
| Glyceryl diisosterate/hydrogenated rosinate | — | — | 10 | — | — | 10 |
| Heavy liquid isoparaffin | — | — | — | 10 | 10 | 10 |
| Methylphenyl polysiloxane | — | — | — | — | 10 | — |
| D & C red No. 7 calcium lake | 5 | 5 | 5 | 5 | 5 | 5 |
| Spreadability | ○ | ○ | Δ | X | ○ | X |
| Gloss | X | ⊙ | ⊙ | ⊙ | ○ | ⊙ |
| Smell | ○ | X | X | X | X | X |

Heavy liquid isoparaffin means having a mean molecular weight of 1000 (Unless the annotation exists in the following.)

Table 1 shows that Comparative example 1 of the composition for lip rouge that does not contain lanolin as the gloss component is inferior in gloss, although it has no odor problem. On the other hand, Comparative examples 2 to 6 of the composition for lip rouge have a problem with smell associated with degradation, although they are excellent in terms of gloss. Accordingly, the conventional composition for lip rouge containing a plentiful amount of lanolin that is not suited to preservation over long period of time.

Component (Glyceryl Diisostearate/Hydrogenated Rosinate Addition Composition)

Thereupon, the inventors studied in order to obtain a composition for lip rouge is excellent in gloss equivalent to a composition containing sufficient lanolin. In Table 2 and Table 3, the composition and the test results of the compositions for lip rouge that the inventors obtained with this process are shown.

TABLE 2

| Raw Material | Comp. Ex. 7 | Comp. Ex. 8 | Comp. Ex. 9 | Work. Ex. 1 | Work. Ex. 2 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylbexanoate | to 100 | to 100 | to 100 | to 100 | to 100 |
| Macdemia nut oil | 10 | 10 | 10 | 10 | 10 |
| Glyceryl diisostearate/hydrogenated rosinate | 10 | 10 | 20 | 10 | 20 |
| Heavy liquid isoparaffin | — | — | — | 10 | 20 |
| Methylphenyl polysiloxane | — | 10 | 20 | — | — |
| D & C red No. 7 calcium lake | 5 | 5 | 5 | 5 | 5 |
| Spreadability | X | ○ | ○ | ○ | ⊙ |
| Gloss | ○ | Δ | Δ | ○ | ⊙ |
| Smell | ○ | ○ | ○ | ○ | ○ |

Table 2 shows that the composition for lip rouge of Working example 1 and 2 of the present invention which contain all of the glyceryl diisostearate/hydrogenated rosinate, the heavy liquid isoparaffin and the methylphenyl polysiloxane are excellent in 3 points of spreadability, gloss, smell. The composition for lip rouge of this invention has achieved the gloss equivalent to lanolin. This is shown by comparison with Table 1.

On the other hand, it is shown that Comparative example 7 that does not include the methylphenyl polysiloxane is inferior in terms of spreadability. Also, Comparative example 8 and Comparative example 9 where the methylphenyl polysiloxane of the component of Working example 1 and 2 was changed into dimethyl polysiloxane of the same silicone oil were inferior in terms of gloss. Also, in case of the composition for lip rouge that used ester oil or liquid petrolatum instead of methylphenyl polysiloxane, the gloss had a tendency to become unsatisfactory similarly, although it is not shown in the above table.

Accordingly, it is understood that only the methylphenyl polysiloxane improves spreadability without dropping gloss.

Next, the results of study with regard to the components other than silicone oil are shown in Table 3.

TABLE 3

| Raw Material | Comp. Ex. 10 | Comp. Ex. 11 | Work. Ex. 3 | Work. Ex. 4 | Test Ex. 5 | Test Ex. 6 |
|---|---|---|---|---|---|---|
| Ceresin wax | 12 | 12 | 12 | 12 | 12 | 12 |
| Carnauba wax | 1 | 1 | 1 | 1 | 1 | 1 |
| Glyceryl tri-2-ethylhexanoate | to 100 | to 100 | to 100 | to 100 | to 100 | to 100 |
| Lanolin | — | 5 | 5 | 5 | — | — |
| Macdemia nut oil | 10 | 10 | 10 | 10 | 10 | 10 |
| Glyceryl diisosterate/hydrogenated rosinate | — | — | 10 | 10 | 10 | 10 |
| Heavy liquid isoparaffin | 20 | — | 10 | 20 | 20 | 20 |
| (Average molecular weight) | (1000) | (—) | (1000) | (1000) | (2000) | (4000) |
| Methylphenyl polysiloxane | 10 | — | 10 | 20 | 20 | 20 |

TABLE 3-continued

| Raw Material | Comp. Ex. 10 | Comp. Ex. 11 | Work. Ex. 3 | Work. Ex. 4 | Test Ex. 5 | Test Ex. 6 |
|---|---|---|---|---|---|---|
| D & C red No. 7 calcium lake | 5 | 5 | 5 | 5 | 5 | 5 |
| Spreadability | Δ | ○ | ○ | ⊚ | ⊚ | Δ |
| Gloss | Δ | X | ○ | ⊚ | ⊚ | ⊚ |
| Smell | ○ | ○ | ○ | ○ | ○ | ○ |

In Table 3, it is shown that the composition of Comparative example 10 that lacked the component of glyceryl diisostearate/hydrogenated rosinate from the indispensable components of the present invention was not sufficient in terms of spreadability and gloss. Furthermore, although it is not shown in above Table 3, the composition that lacked the component of the heavy liquid isoparaffin was insufficient in terms of spreadability and of gloss similarly.

Also, The composition for lip rouge of Working example 3 and Working example 4 containing a small amount of lanolin do not have a problem in the evaluation of smell (preservation stability over a long period of time). Accordingly, there was not a problem to about 5 wt % of lanolin. However, as shown in Comparative example 11, about 5 wt % of lanolin was unable to give gloss to the composition for lip rouge.

Accordingly, as the result of above-mentioned Table 2 and Table 3, it is shown that only the composition containing glyceryl diisostearate/hydrogenated rosinate and heavy liquid isoparaffin and methylphenyl polysiloxane is excellent in all 3 points for lip rouge which were spreadability, gloss, and smell.

Also, from the evaluation result of Test example 1 of mean molecular weight 2000 of heavy liquid isoparaffin and Test example 1 of 4000, in consideration of point of spreadability, it is shown that the mean molecular weight of heavy liquid isoparaffin in the present invention, preferably about 3000.

Amount of Glyceryl Diisostearate/Hydrogenated Rosinate (Glyceryl Diisostearate/Hydrogenated Rosinate Addition Composition)

Next, the amount of the glyceryl diisostearate/hydrogenated rosinate was studied. The results are shown in Table 4.

TABLE 4

| Raw Material | Test Ex. 3 | Test Ex. 4 | Test Ex. 5 | Test Ex. 6 | Test Ex. 7 | Test Ex. 8 |
|---|---|---|---|---|---|---|
| Ceresin wax | 12 | 12 | 12 | 12 | 12 | 12 |
| Carnauba wax | 1 | 1 | 1 | 1 | 1 | 1 |
| Glyceryl tri-2-ethylhexanoate | to 100 | to 100 | to 100 | to 100 | to 100 | to 100 |
| Macdemia nut oil | 10 | 10 | 10 | 10 | 10 | 10 |
| Glyceryl diisostearate/hydrogenated rosinate | 5 | 5 | 10 | 20 | 40 | 40 |
| Heavy liquid isoparaffin | 5 | 10 | 20 | 10 | 10 | 20 |
| Methylphenyl polysiloxane | 5 | 10 | 20 | 20 | 20 | 10 |
| D & C red No. 7 calcium lake | 5 | 5 | 5 | 5 | 5 | 5 |
| Spreadability | ○ | ○ | ⊚ | ○ | Δ | Δ |
| Gloss | Δ | ○ | ⊚ | ⊚ | ⊚ | ⊚ |
| Smell | ○ | ○ | ○ | ○ | ○ | ○ |

In Table 4, it is shown that the amount of glyceryl diisostearate/hydrogenated rosinate is preferably about 5 to 20 wt %. Furthermore, when Test example 7 and Test example 8 are compared, it is shown that Test example 8 of much greater amount of heavy liquid isoparaffin has heavy spreadability. Also, Test example 3 is the example of little amount of heavy liquid isoparaffin and methylphenyl polysiloxane. When there are small amounts of other components like Test example 3, and the amount of glyceryl diisostearate/hydrogenated rosinate is 5 wt % it sometimes has inferior gloss etc.

Amount of Heavy Liquid Isoparaffin (Glyceryl Diisostearate/Hydrogenated Rosinate Addition Composition)

Next, the amount of the heavy liquid isoparaffin was studied. The results are shown in Table 5.

TABLE 5

| Raw Material | Test Ex. 9 | Test Ex. 10 | Test Ex. 11 | Test Ex. 12 | Test Ex. 13 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylhexanoate | to 100 | to 100 | to 100 | to 100 | to 100 |
| Macdemia nut oil | 10 | 10 | 10 | 10 | 10 |
| Glyceryl diisostearate/hydrogenated rosinate | 5 | 20 | 20 | 20 | 10 |
| Heavy liquid isoparaffin | 5 | 10 | 20 | 30 | 40 |
| Methylphenyl polysiloxane | 10 | 20 | 20 | 20 | 20 |
| D & C red No. 7 calcium lake | 5 | 5 | 5 | 5 | 5 |
| Spreadability | ○ | ○ | ⊚ | ⊚ | Δ |
| Gloss | Δ | ⊚ | ⊚ | ⊚ | ⊚ |
| Smell | ○ | ○ | ○ | ○ | ○ |

In Table 5, it is shown that gloss is inferior in case of compounding less than 10 wt % of the heavy liquid isoparaffin (Test example 9). It is shown that spreadability becomes unsatisfactory in case of compounding more than 30 wt % (Test example 13). Accordingly, it is shown that the amount of the heavy liquid isoparaffin is preferably 10 to 30 wt %.

Amount of Methylphenyl Polysiloxane (Glyceryl Diisostearate/Hydrogenated Rosinate Addition Composition)

Next, the amount of the methylphenyl polysiloxane was studied. The results are shown in Table 6.

TABLE 6

| Raw Material | Test Ex. 14 | Test Ex. 15 | Test Ex. 16 | Test Ex. 17 | Test Ex. 18 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylhexanoate | to 100 | to 100 | to 100 | to 100 | to 100 |
| Macdemia nut oil | 10 | 10 | 10 | 10 | 10 |
| Glyceryl diisostearate/ hydrogenated rosinate | 5 | 10 | 10 | 10 | 10 |
| Heavy liquid isoparaffin | 10 | 10 | 20 | 20 | 20 |
| Methylphenyl polysiloxane | 5 | 10 | 20 | 30 | 40 |
| D & C red No. 7 calcium lake | 5 | 5 | 5 | 5 | 5 |
| Spreadability | Δ | ○ | ◉ | ○ | ○ |
| Gloss | ○ | ○ | ◉ | ◉ | Δ |
| Smell | ○ | ○ | ○ | ○ | ○ |

In Table 6, it is shown that spreadability is inferior when compounding less than 10 wt % of the methylphenyl polysiloxane. It is shown that gloss becomes unsatisfactory when compounding more than 30 wt %. Accordingly, it is shown that the amount of the methylphenyl polysiloxane is preferably 10 to 30 wt %.

The inventors have obtained a composition for lip rouge that excels in the gloss equivalent to lanolin, by using a hydroxy acid ester instead of said glyceryl diisostearate/hydrogenated rosinate, and without using glyceryl diisostearate/hydrogenated rosinate. In the following, the development process of this composition for lip rouge will be explained.

Prior Art (Hydroxy Acid Ester Addition Composition)

First of all, the conventional composition for lip rouge of the following Table 7 is prepared and each of the above-mentioned tests was carried out. The composition of Table 7 includes the examples of the conventional composition for lip rouge that contains lanolin as a gloss component. Comparative example 12 and 13 are the composition for lip rouge containing lanolin as a gloss component.

TABLE 7

| Raw Material | Comp. Ex. 2 | Comp. Ex. 12 | Comp. Ex. 13 |
|---|---|---|---|
| Ceresin wax | 12 | 12 | 12 |
| Carnauba wax | 1 | 1 | 1 |
| Glyceryl tri-2-ethylhexanoate | to 100 | to 100 | to 100 |
| Macdemia nut oil | 10 | 10 | 10 |
| Lanolin | 10 | — | — |
| 2-hexyl decyl · 12-hydroxy octa decanoate | — | — | 10 |
| Heavy liquid isoparaffin | — | 10 | — |
| Methylphenyl polysiloxane | — | — | 10 |
| Dimethyl polysiloxane | — | — | — |
| D&C red No.7 calcium lake | 5 | 5 | 5 |
| Spreadability | ○ | X | X |
| Gloss | ◉ | ○ | ○ |
| Smell | X | ○ | ○ |

Heavy liquid isoparaffin: mean molecular weight 1000(The following thing is same unless a notation specially.)

In Table 7, it is shown that Comparative example 2 of the composition for lip rouge containing lanolin as the gloss component is inferior smell, although it has no problem in the improvement of gloss and feel of use. Also, although the composition for rouge for the lip of Comparative example 12 containing the heavy liquid isoparaffin is excellent in smell associated with degradation, the gloss is not complete and there is a problem with the feeling. It is shown that the Comparative example 13 containing the heavy liquid isoparaffin and the hydroxy acid ester was a problem still in terms of feeling.

Component (Hydroxy Acid Ester Addition Composition)

Thereupon, the inventors worked to obtain a composition for lip rouge which is excellent in gloss similar to lanolin and which as contains little lanolin as possible. In the following Table 8, the compositions and the test results of the compositions for lip rouge that the inventors obtained with are shown.

TABLE 8

| Raw material | Comp. Ex. 14 | Work. Ex. 5 |
|---|---|---|
| Ceresin wax | 12 | 12 |
| Carnauba wax | 1 | 1 |
| Glyceryl tri-2-ethylhexanoate | to 100 | to 100 |
| Macdemia nut oil | 10 | 10 |
| Lanolin | 10 | 10 |
| 2-hexyl decyl · 12-hydroxy octa decanoate | 10 | 10 |
| Heavy liquid isoparaffin | 10 | 10 |
| Methylphenyl polysiloxane | — | 10 |
| Dimethyl polysiloxane | 10 | — |
| D&C red No.7 calcium lake | 5 | 5 |
| Spreadability | ○ | ○ |
| Gloss | Δ | ○ |
| Smell | ○ | ○ |

In Table 8, in the composition for lip rouge of Working Example 5 of the present invention containing all of the hydroxy acid ester, the heavy liquid isoparaffin and the methylphenyl polysiloxane is excellent in spreadability, gloss, and smell.

Also, in the Comparative Example 14 in the case where the methylphenyl polysiloxane of the component of Working Example 5 was changed to dimethyl polysiloxane of the same silicone oil content, the gloss was inferior. Also, in case of the composition for lip rouge that used ester oil or liquid petrolatum instead of methylphenyl polysiloxane, the gloss had a tendency to become unsatisfactory similarly, although it is not shown in Table 8.

Accordingly, it is understood that only the composition for lip rouge containing methylphenyl polysiloxane improves spreadability without reducing gloss.

Amount of Hydroxy Acid Ester (Hydroxy Acid Ester Addition Composition)

Next, the amount of the hydroxy acid ester was studied. The results are shown in Table 9.

TABLE 9

| Raw Material | Test Ex. 19 | Test Ex. 20 | Test Ex. 21 | Test Ex. 22 | Test Ex. 23 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylhexanoate | to 100 | to 100 | to 100 | to 100 | to 100 |
| Macdemia nut oil | 10 | 10 | 10 | 10 | 10 |
| Lanolin | — | — | — | — | — |

TABLE 9-continued

| Raw Material | Test Ex. 19 | Test Ex. 20 | Test Ex. 21 | Test Ex. 22 | Test Ex. 23 |
|---|---|---|---|---|---|
| 2-hexyl decyl. 12-hydroxy octa decanoate | 5 | 10 | 20 | 30 | 40 |
| Heavy liquid isoparaffin | 10 | 10 | 10 | 10 | 10 |
| Methylphenyl polysiloxane | 10 | 10 | 10 | 10 | 10 |
| Dimethyl polysiloxane | — | — | — | — | — |
| D & C red No. 7 calcium lake | 5 | 5 | 5 | 5 | 5 |
| Spreadability | ○ | ⊙ | ⊙ | ⊙ | Δ |
| Gloss | ○ | ○ | ⊙ | ⊙ | ⊙ |
| Smell | ○ | ○ | ○ | ○ | ○ |

In Table 9, it is shown that the amount of the hydroxy acid ester is preferably about 5 to 30 wt %.

Amount of Heavy Liquid Isoparaffin (Hydroxy Acid Ester Addition Composition)

Next, the heavy liquid isoparaffin has been studied. The results are shown in Table 10.

TABLE 10

| Raw Material | Test Ex. 24 | Test Ex. 25 | Test Ex. 26 | Test Ex. 27 | Test Ex. 28 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylhexanoate | to 100 | to 100 | to 100 | to 100 | to 100 |
| Macdemia nut oil | 10 | 10 | 10 | 10 | 10 |
| Lanolin | — | — | — | — | — |
| 2-hexyl decyl. 12-hydroxy octa decanoate | 10 | 10 | 10 | 10 | 10 |
| Heavy liquid isoparaffin | 5 | 10 | 20 | 30 | 40 |
| Methylphenyl polysiloxane | 10 | 10 | 10 | 10 | 10 |
| Dimethyl polysiloxane | — | — | — | — | — |
| D & C red No. 7 calcium lake | 5 | 5 | 5 | 5 | 5 |
| Spreadability | ○ | ○ | ⊙ | ⊙ | Δ |
| Gloss | Δ | ○ | ⊙ | ⊙ | ⊙ |
| Smell | ○ | ○ | ○ | ○ | ○ |

In Table 10, it is shown that point of gloss is inferior in when there was less than 10 wt % of the heavy liquid isoparaffin. It is understood that spreadability becomes unsatisfactory when there is more than 30 wt % (heavy liquid isoparaffin). Accordingly, it is shown that the amount of the heavy liquid isoparaffin is preferably 10 to 30 wt %.

Amount of Methylphenyl Polysiloxane (Hydroxy Acid Ester Addition Composition)

Next, the amount of the methylphenyl polysiloxane was studied. The results are shown in Table 11.

TABLE 11

| Raw Material | Test Ex. 29 | Test Ex. 30 | Test Ex. 31 | Test Ex. 32 | Test Ex. 33 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylhexanoate | to 100 | to 100 | to 100 | to 100 | to 100 |
| Macdemia nut oil | 10 | 10 | 10 | 10 | 10 |
| Lanolin | — | — | — | — | — |
| 2-hexyl decyl. 12-hydroxy octa decanoate | 10 | 10 | 10 | 10 | 10 |

TABLE 11-continued

| Raw Material | Test Ex. 29 | Test Ex. 30 | Test Ex. 31 | Test Ex. 32 | Test Ex. 33 |
|---|---|---|---|---|---|
| Heavy liquid isoparaffin | 10 | 10 | 10 | 10 | 10 |
| Methylphenyl polysiloxane | 5 | 10 | 20 | 30 | 40 |
| Dimethyl polysiloxane | — | — | — | — | — |
| D & C red No. 7 calcium lake | 5 | 5 | 5 | 5 | 5 |
| Spreadability | Δ | ⊙ | ⊙ | ⊙ | ⊙ |
| Gloss | ○ | ○ | ○ | ○ | Δ |
| Smell | ○ | ○ | ○ | ○ | ○ |

In Table 11, it is shown that spreadability is inferior when there is less than 10 wt % of methylphenyl polysiloxane. It is shown that gloss becomes unsatisfactory when there is more than 30 wt %. Accordingly, it is shown that the amount of the methylphenyl polysiloxane is preferably 10 to 30 wt %.

Kind of Hydroxy Acid Ester (Hydroxy Acid Ester Addition Composition)

Next, the kind of the hydroxy acid ester was studied. The results are shown in Table 12.

TABLE 12

| Raw Material | Work. Ex. 6 | Work. Ex. 7 | Work. Ex. 8 | Work. Ex. 9 | Work. Ex. 10 |
|---|---|---|---|---|---|
| Ceresin wax | 12 | 12 | 12 | 12 | 12 |
| Carnauba wax | 1 | 1 | 1 | 1 | 1 |
| Glyceryl tri-2-ethylhexanoate | to 100 | to 100 | to 100 | to 100 | to 100 |
| Isolauryl hydrxy myristate | 10 | — | — | — | — |
| 2-hexyl decyl. hydroxy eicosanoate | — | 10 | — | — | — |
| 2-heptyl undecyl. 12-hydroxy octadecanoate | — | — | 10 | — | — |
| 2-octyl dodecyl. 12-hydroxy octadecanoate | — | — | — | 10 | — |
| *Hydroxy acid esterΔ | — | — | — | — | 10 |
| Heavy liquid isoparaffin | 10 | 10 | 10 | 10 | 10 |
| Methylphenyl polysiloxane | 10 | 10 | 10 | 10 | 10 |
| D & C red No. 7 calcium lake | 5 | 5 | 5 | 5 | 5 |
| Spreadability | ○ | ○ | ○ | ○ | ○ |
| Gloss | ○ | ○ | ○ | ○ | ○ |
| Smell | ○ | ○ | ○ | ○ | ○ |

(*Hydroxy acid ester A is the ester of 12- Hydroxy acid oligomer and 12-hydroxy stearyl alcohol)

In Table 12, it is shown that the hydroxy acid esters of Working Examples 6 to 10 are excellent in spreadability, gloss, and smell.

The composition for lip rouge of the present invention contains a glyceryl diisostearate/hydrogenated rosinate and/optionally a hydroxy acid ester, a heavy liquid isoparaffin, and a methylphenyl polysiloxane. Accordingly, the composition for lip rouge of the present invention is excellent with a light feeling has good gloss and stable for a long time

What is claimed is:

1. A composition for lip rouge containing:

a glyceryl diisostearate/hydrogenated rosinate, a heavy liquid isoparaffin, a methylphenyl polysiloxane, and optionally, a hydroxy acid ester.

2. The composition for lip rouge according to claim 1, wherein said composition contains:

5 to 20 wt % of the glyceryl diisostearate/hydrogenated rosinate, 10 to 30 wt % of the heavy liquid isoparaffin, and 10 to 30 wt % of the methylphenyl polysiloxane.

3. The composition for lip rouge according to claim 1, wherein said composition contains:

5 to 30 wt % of the hydroxy acid ester, 10 to 30 wt % of the heavy liquid isoparaffin, and 10 to 30 wt % of the methylphenyl polysiloxane.

4. The composition for lip rouge according to claim 1, wherein said hydroxy acid ester is composed of an aliphatic alcohol of carbon number 12 to 20, and a hydroxy acid of carbon number 12 to 20.

5. The composition for lip rouge according to claim 1, wherein said hydroxy acid ester is composed of 12-hydroxystearic acid of the hydroxy acid, and 2-heptyl undecanol of the aliphatic alcohol.

6. The composition for lip rouge according to claim 1, wherein said heavy liquid isoparaffin's mean molecular weight is 500 to 3000.

7. A composition for lip rouge according to claim 1, wherein said composition is in the form of a make-up product which is a lip rouge.

\* \* \* \* \*